United States Patent [19]

Hiraide et al.

[11] Patent Number: 5,736,099
[45] Date of Patent: Apr. 7, 1998

[54] TEST PLATES FOR AGGLUTINATION TEST AND PRODUCTION PROCESS THEREOF

[75] Inventors: Tsuneo Hiraide; Tetsuro Ogawa; Ayumi Mitoh, all of Tokyo; Tadahiko Kitano, 954-30, Yokokawamachi, Hachioji-shi, Tokyo; Mikio Nakayama, 11-25, Saginumadai 3-chome, Narashino-shi, Chiba-ken, all of Japan

[73] Assignees: Asahi Kogaku Kogyo Kabushiki Kaisha; Tadahiko Kitano, both of Tokyo; Mikio Nakayama, Chiba-ken, all of Japan

[21] Appl. No.: 579,584

[22] Filed: Dec. 28, 1995

[30] Foreign Application Priority Data

Dec. 28, 1994 [JP] Japan ................... 6-328789

[51] Int. Cl.$^6$ ............................. G01N 33/53
[52] U.S. Cl. ................... 422/57; 422/102; 436/69; 427/338
[58] Field of Search ................ 422/102, 55, 57; 436/69; 427/337–338

[56] References Cited

U.S. PATENT DOCUMENTS 5,085,781  2/1992  Tsuru et al. .
5,418,136  5/1995  Miller et al. ................... 422/55
5,540,995  7/1996  Kitano et al. ................... 428/407

FOREIGN PATENT DOCUMENTS 5249506  10/1993  Japan .

OTHER PUBLICATIONS

Fahnestock et al., "Gene for an Immunoglobin–Binding Protein from a Group G Streptococcus", J. of Bacteriology, Sep. 1986, pp. 870–880.

Alexander et al., "Thermodynamic Analysis of the Folding of the Streptococcal Protein G IgG–Binding Domains B1 and B2: . . . " Biochemistry, 1992, 31, pp. 3597–3603.

Primary Examiner—Lyle A. Alexander
Attorney, Agent, or Firm—Greenblum & Bernstein, P.L.C.

[57] ABSTRACT

A test plate for an agglutination test which comprises a plate with a plurality of wells formed thereon, each of the wells having adhered to a surface thereof a protein A and/or a protein G. The agglutination test plate, according to the present invention, when used in an agglutination test, can ensure a clear judgment concerning the formation of an agglutinative image or a non-agglutinative image, along with a good determination sensitivity. A process for the production of such an agglutination test plate is also provided.

18 Claims, 2 Drawing Sheets

TEST PLATES FOR AGGLUTINATION TEST AND PRODUCTION PROCESS THEREOF

BACKGROUND OF THE INVENTION

1. Field of the Invention

The present invention relates to a test plate for use in an agglutination test which can be utilized when diagnosing, for example, diseases, and may be performed with reference to the agglutination reaction based on an antigen-antibody reaction.

2. Description of the Related Art

Hitherto, an agglutination reaction process has been used to determine the amount or level of certain antibodies contained in a test fluid, such as, a serum, body fluid, etc. In this process, agglutinative composite particles, for example, particles of gelatine, kaolin, synthetic polymer, and other materials immobilized with a predetermined antigen, have been used as a test medium. Using these agglutinative composite particles, a test plate having wells is produced for use in judging the agglutination reaction. Into these wells a test fluid added to form an array of the diluted test fluid. Judgment regarding the agglutination reaction is made with reference to the state of the agglutinative product in the wells. Namely, when an agglutination reaction occurs, i.e., the reaction is positive, an agglutinative image can be observed as a mat-like agglutinated product uniformly adhered to a side wall surface of the wells. When no agglutination occurs, i.e., when the reaction is negative, no reaction product adheres to the side wall of the wells, but instead the product slides down from the side wall to the bottom part of the wells to form a circular button-like aggregate.

The prior art agglutination test plates suffer from some drawbacks, however, such as the formation of an intermediate agglutinative image insufficient to clearly judge as either a "positive" or "negative" reaction. Difficulties also arise when using the agglutination reaction process due to, for example, an unsuitable shape or configuration of the wells in the test plate or lower determination sensitivity when compared with other determination processes, etc.

SUMMARY OF THE INVENTION

One object of the present invention is to provide an agglutination test plate which, when used in an agglutination test, can ensure a clear judgment concerning whether the formed image is an agglutinative or a non-agglutinative image, along with a good determination sensitivity.

Another object of the present invention is to provide a process for the production of such an agglutination test plate.

Further objects of the present invention will be appreciated from the descriptions set forth below with regard to the preferred embodiments thereof.

In one aspect of the present invention, there is provided a test plate for an agglutination test which comprises a plate with a plurality of wells formed thereon, each of the wells having adhered to a surface thereof a protein A and/or a protein G.

In another aspect of the present invention, there is provided a process for the production of a test plate for an agglutination test. The process comprises the following steps:
 providing a test plate with a plurality of wells formed thereon,
 applying a small amount of a protein solution containing protein A and/or protein G to each of the wells of the plate,
 removing the applied protein solution from the wells, and
 drying the plate to obtain a test plate comprising wells wherein a surface of each well has protein A and/or protein G adhered thereto.

The present disclosure relates to subject matter contained Japanese Patent Application No. 6-328789 (filed on Dec. 28, 1994) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENTS

Figure 1:
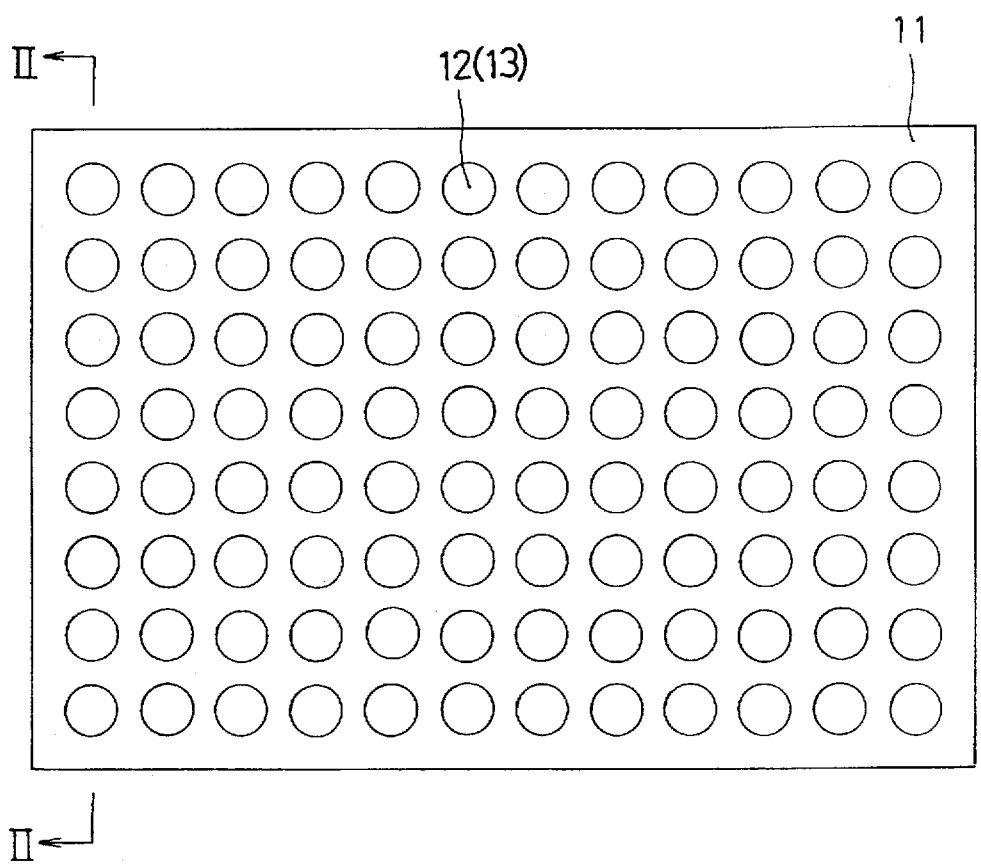
FIG. 1 is a schematic view of a test plate used in the present invention.

FIG. 1 shows a test plate 11 for an agglutination test, according to an aspect of the present invention, characterized in that the plate has a plurality of wells 12 (13), in this case 96 wells (8×12), formed thereon. In the solution applied to the wells, protein A and protein G may be used separately or in combination. It is easily possible to adhere protein A and/or protein G onto an inner surface of the wells of the agglutination test plate 11, and only a small amount of the adhered protein A and/or protein G is necessary to form an agglutinative image capable of establishing a clear judgment as to whether the agglutination reaction is positive or negative.

Further, the method of producing the agglutination test plate, according to the present invention, is characterized by dropping a small amount of a protein A- and/or protein G-containing solution into each of the wells 12 (13) of the test plate, and drying the test plate after removing the protein solution from the wells.

Figure 2A:
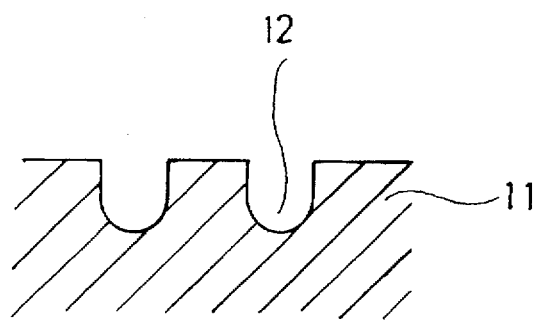
FIG. 2A is a side view of the test plate shown in FIG. 1, having wells with a curved bottom portion; and, FIG. 2B is a side view of the test plate shown in FIG. 1, having wells with a V-shaped bottom portion.
Figure 2B:
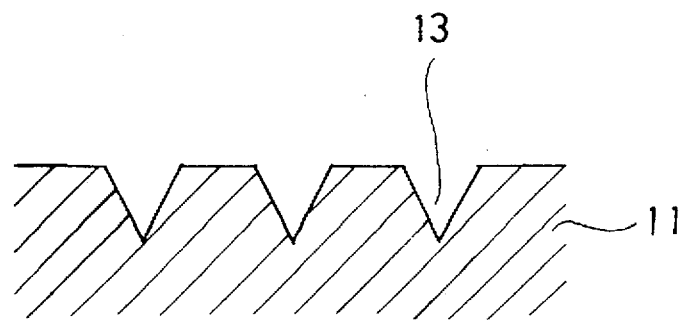

In the practice of the present invention, the type of plate chosen for use as the test plate is not restricted, and, accordingly, may have any desired shape and may be formed from any suitable material. FIGS. 2A and 2B show side views of the test plate 11 having U-shaped wells 12 and V-shaped wells 13, respectively, taken along the line II—II in FIG. 1. It should be noted that the plate may be formed from any plastic, such as, polystyrene, polypropylene, polyvinylchloride etc., or if desired, from metal or ceramic. Further, the number and arrangement of wells formed on the test plate 11 is not limited to that shown in FIG. 1, and may be any number or arrangement suitable for performing the test(s) required.

A satisfactory determination can be made, as to whether the agglutination reaction is positive or negative, if only a trace of the adhered protein A and/or protein G can be retained on the well surface, after a small amount of the protein A- and/or protein G-containing solution has been dropped into the wells and then removed from the wells.

Generally, the amount of the protein solution to be applied to each well is sufficient, if the applied solution can fill a V-shaped bottom portion 13, or a curved bottom portion 12, of the well of the test plate. More particularly, if the wells of the test plate have a capacity of 0.3 ml, a satisfactory amount of the protein A- and/or protein G-containing solution to be applied to the wells is about 0.05 ml.

The protein A- and/or protein G-containing solution used in the practice of the present invention is a solution of protein A and/or protein G dissolved in a solvent, such as, water, physiological salt buffer solution (PBS or the like), physiological saline, etc. The concentration of the protein A and/or protein G in the solution is not restricted and may vary widely depending upon various factors; however, the concentration of the proteins is preferably $1.0 \times 10^{-6}$ mg/ml or more, and more preferably, in the range $1.0 \times 10^{-3}$ mg/ml to $1.0 \times 10^{-1}$ mg/ml. Note that the above concentration is the sum of protein A and protein G, if both proteins are contained in the same solution.

In the production of the agglutination test plate, according to the present invention, it is preferred that a solution containing protein A and/or protein G be dropped in the wells of the test plate. The protein solution is left at rest in the wells for a predetermined time, preferably, a few minutes or more, before being removed. The length of time the protein solution-carrying wells are left at rest can vary depending upon the concentration of protein A and/or protein G in the protein solution, i.e., a concentration of either one or both of protein A and protein G. This time may be shortened to substantially zero, if a higher concentration ($1.0 \times 10^{-3}$ mg/ml or more) of protein A and/or protein G is contained in the protein solution.

Further, it is preferred that after dropping the protein A- and/or protein G-containing solution into each well of the plate, the solution be poured out from the wells, and then the plate be washed with water, physiological salt solution, physiological saline or the like, to remove the remaining loose protein A and/or protein G from the wells (i.e., that protein that has not adhered to the wells). The washed plate is then dried, to thereby produce a test plate for the agglutination test.

Drying of the plate may be carried out naturally or with the assistance of heat to aid in the evaporation of water from the surface of the plate.

The thus produced agglutination test plate contains protein A and/or protein G uniformly adhered to a surface of each well of the plate. The adhered protein can be stably stored for an extended period of time at room temperature. For example, the test plate with the adhered protein could be used in the agglutination test, without suffering from any deterioration in efficiency, for up to 7 days or more, after storage at a temperature of between 4° to 25° C.

Protein A and protein G can specifically bond to Fc fragments of human immunoglobulin G (IgG), for example. So, if the test fluid containing such antibody is dropped into the wells of the test plate, according to the present invention, a specifical bond is produced between the Fc fragments of the antibody in the test fluid and the protein A and/or protein G uniformly adhered to a surface of the wells. The antibody in the specifical bond, if it reacts with any antigen which is subsequently dropped into the wells for the purpose of agglutination, can produce a mat-like aggulutination image extending over the wall surface of the wells.

The antigen used in the above antigen-antibody reaction can be used in any conventional form, however, in view of the operability and reproducibility of the same, the antigen can be preferably used in the form of antigen-immobilized agglutinative composite particles. Particles suitable as carriers of the agglutinative composite particles include, for example, ceramics/polymer composite particles or particles of latex, gelatine, kaolin, synthetic polymer and other materials. For example, agglutinative composite particles comprising the ceramics/polymer composite particles having the immobilized antigen can be produced by coating a surface of the polymer particles with a calcium phosphate compound to form a ceramics-coated particulate polymer composite, the polymer particles or the whole of which may be dyed, adsorbing and immobilizing an antigen to the particulate polymer composite, and treating the not-adsorbed sites of the polymer composite with a blocking agent, as is disclosed in the specification of Japanese Patent Application No. 5-249506, for instance. For the particulate polymer composite used herein, it is preferred to use one produced by physically impinging particles of the calcium phosphate compound against the polymer particles, thereby forming a coating of the calcium phosphate compound over a surface of the polymer particles.

According to the present invention, it becomes possible in the diagnosis of diseases, with reference to the agglutination reaction based on the antigen-antibody reaction, to clearly ascertain whether an agglutinative image was formed or not based upon the agglutination reaction. Additionally, the agglutination test plate is produced simply and has a good sensitivity. Further, since it has an excellent storage stability, the agglutination test plate of the present invention can exhibit its remarkably improved functions, for an extended period of time, even if stored at room temperature.

The present invention will be further described with reference to some working examples thereof; however, it should be noted that the working examples do not restrict the scope of the present invention.

EXAMPLE 1 (reference example)

Preparation of Antigen-Immobilized Agglutinative Composite Particles

A. Preparation of Particles of Polymer Composite 50 g of nylon beads having an average particle diameter of 5 microns and a density of 1.03 g/cm$^3$, dyed with an anthraquinone disperse dye- MITSUI ML Colors ML red VF-2 (commercially available from Mitsui Toatsu Senryou), and 7.5 g of particles of hydroxyapatite having a Ca/P ratio of 1.67, an average particle diameter of 5 microns, a specific surface area of 45 m$^2$/g, an apparent density of 1.8 g/cm$^3$ and a pore size of 600 Å, were added to a hybridization machine- Nara Hybridization System NHS-1 (having a rated power of 5.5 kw and a rated current of 23 A, commercially available from Nara Kikai Seisakusho). The hybridization machine was operated at 8000 revolutions per minute (rpm) at between 32° and 50° C. for 5 minutes. Nylon beads having a hydroxyapatite coating applied to a surface thereof were thus obtained. The resulting composite particles had an average particle diameter of 5.8 microns, a density of 1.13 g/cm$^3$ and a pore size of 600 Å.

B. Preparation of Antigen-Immobilized Agglutinative Composite Particles 10 ml of a virus-floating liquid containing 2000 titers of A-type influenza virus was added to 0.1 g of the composite particles produced in the above step. After thorough stirring, the mixture was centrifuged to remove an excess amount of the influenza virus. Then, 10 ml of a 0.1% glutaraldehyde solution was added to the mixture to immobilize the virus adsorbed onto the composite particles. After immobilization of the virus, 5 ml of a blocking agent containing casein, trade name "Block Ace" (commercially available from Snow Brands Milk Products Co., Ltd.) was added to the mixture. It was thoroughly stirred, and then centrifuged to remove an excess amount of Block Ace. Then, 20 ml of physiological salt buffer solution (PBS) was added. Influenza virus-immobilized composite particles were thus produced.

EXAMPLE 2 (reference example)

Preparation of Antigen-Immobilized Agglutinative Composite Particles

A. Preparation of Particles of Polymer Composite 50 g of nylon beads having an average particle diameter of 5 microns and a density of 1.03 g/cm$^3$, dyed with an anthraquinone disperse dye- MITSUI ML Colors ML blue VF (commercially available from Mitsui Toatsu Senryou), and 7.5 g of particles of hydroxyapatite having a Ca/P ratio of 1.67, an average particle diameter of 5 microns, a specific surface area of 45 m$^2$/g, an apparent density of 1.8 g/cm$^3$ and a pore size of 600 Å, were added to a hybridization machine- Nara Hybridization System NHS-1 (having a rated power of 5.5 kw and a rated current of 23 A, commercially available from Nara Kikai Seisakusho). The hybridization machine was operated at 8000 revolutions per minute (rpm) at between 32° and 50° C. for 5 minutes. Nylon beads having a hydroxyapatite coating applied to a surface thereof were thus obtained. The resulting composite particles had an average particle diameter of 5.8 microns, a density of 1.13 g/cm$^3$ and a pore size of 600 Å.

B. Preparation of Antigen-Immobilized Agglutinative Composite Particles 10 ml of a virus-floating liquid containing 4000 titers of the Japanese Bemcephalitis virus was added to 0.1 g of the composite particles produced in the above step. After thorough stirring, the mixture was centrifuged to remove an excess amount of the virus. Then, 10 ml of a 0.1% glutaraldehyde solution was added to the mixture to immobilize the virus adsorbed onto the composite particles. After immobilization of the virus, 5 ml of a blocking agent containing casein, trade name "Block Ace" (commercially available from Snow Brands Milk Products Co., Ltd.) was added to the mixture. It was thoroughly stirred, and then centrifuged to remove an excess amount of Block Ace. Then, 20 ml of physiological salt buffer solution (PBS) was added. Japanese Bemcephalitis virus-immobilized composite particles were thus produced.

EXAMPLE 3

A. Production of Agglutination Test Plate

A polystyrene plate with 96 U-shaped wells, each having a capacity of 0.3 ml, was provided. To each well of the polystyrene plate, 0.05 ml of a PBS solution containing protein A in a concentration of $1.0\times10^{-6}$ mg/ml was added. After 20 hours, the PBS solution was poured out from the wells of the plate. Then, 0.05 ml of a fresh PBS solution was added to each well and again poured out from the wells to remove the remaining loose protein A from the wall surface of the wells. The plate was dried to produce a protein A-adhered test plate.

The above procedure was repeated by using PBS solutions containing different concentrations of protein A. The protein A concentrations that were also applied were: $1.0\times10^{-5}$ mg/ml, $1.0\times10^{-4}$ mg/ml, $1.0\times10^{-3}$ mg/ml, $1.0\times10^{-2}$ mg/ml, $1.0\times10^{-1}$ mg/ml and 1.0 mg/ml. As a result, a total of seven types of the protein A-adhered test plates were thus produced.

B. Agglutination Test

On each of the protein A-adhered test plates produced in the above step, a rabbit antiserum for the influenza virus used in step B of Example 1, rabbit antiserums for other viruses and a rabbit serum not-infected with a virus were each added to the wells of the plate to make 0.05 ml of the antiserum or serum solution per well, after it was diluted with PBS. Dilution with PBS was repeatedly made so that twice the volume of the antiserum or serum solution was produced after each dilution. After 30 minutes, 0.05 ml of the PBS solution of the influenza virus antigen-immobilized agglutinative composite particles produced in step B of Example 1 was added to each well. No agglutinated image was observed in any of the protein A-adhered test plates containing the rabbit antiserums for other viruses, or rabbit serum not-infected with a virus in the wells thereof. Contrary to this, in the protein A-adhered test plate containing the rabbit antiserum for the influenza virus in the wells thereof, a clear agglutinated image was observed in the wells, until the rabbit antiserum was further diluted with the PBS to make a dilution degree of 32000 times; however, no agglutinated image was observed when the rabbit antiserum was diluted to make a dilution degree of 64000 times or more.

EXAMPLE 4

A. Production of Agglutination Test Plate

A polypropylene plate with 96 U-shaped wells, each having a capacity of 0.3 ml, a polystyrene plate with 96 V-shaped wells, each well having a capacity of 0.3 ml, and a polyvinyl chloride plate with 96 U-shaped wells, each well having a capacity of 0.2 ml, were provided. To each well of each of these plates, 0.05 ml of a PBS solution containing protein A in a concentration of $1.0\times10^{-3}$ mg/ml was added. After 60 minutes, the PBS solution was poured out from the wells of the plate. Then, 0.05 ml of a fresh PBS solution was added to each well and again poured out from the wells to remove the remaining loose protein A from the wall surface of the wells. The plate was dried to produce a protein A-adhered test plate.

B. Agglutination Test

Using the protein A-adhered test plates produced in the above step, the agglutination test was made in a manner similar to that described in step B of Example 3. Satisfactory results, which were substantially the same as those of Example 3, could be obtained.

EXAMPLE 5

A. Production of Agglutination Test Plate

A polystyrene plate with 96 V-shaped wells, each well having a capacity of 0.3 ml, was provided. To each well of the polystyrene plate, 0.05 ml of a PBS solution containing protein A in a concentration of $1.0\times10^{-3}$ mg/ml was added. After one minute, the PBS solution was poured out from the wells of the plate. Then, 0.05 ml of a fresh PBS solution was added to each well and again poured out from the wells to remove the remaining loose protein A from the wall surface of the wells. The plate was dried to produce a protein A-adhered test plate.

The above procedure was repeated by changing the treating time from one minute to 10 minutes, 30 minutes, one hour, 3 hours and 20 hours, respectively. Six types of protein A-adhered test plates were thus produced.

B. Agglutination Test

On each of the protein A-adhered test plates produced in the above step, a rabbit antiserum for the Japanese Bemcephalitis virus used in step B of Example 2, rabbit antiserums for other viruses and a rabbit serum not-infected with a virus were each added to the wells of the plate to make 0.05 ml of the antiserum or serum solution per well, after it was diluted with PBS. The dilution with PBS was repeatedly made so that twice the volume of the antiserum or serum solution was produced after each dilution. After 30 minutes, 0.05 ml of the PBS solution Of the Japanese Bemcephalitis virus antigen-immobilized agglutinative composite particles produced in step B of Example 2 was added to each well. No agglutinated image was observed in any of the protein A-adhered test plates containing the rabbit antiserums for other viruses, or rabbit serum not-infected with a virus in the wells thereof. Contrary to this, in the protein A-adhered test plate containing the rabbit antiserum for the Japanese Bemcephalitis virus in the wells thereof, a clear agglutinated image was observed in the wells, until the rabbit antiserum was further diluted with the PBS to make a dilution degree of 8000 times; however, no agglutinated image was observed when the rabbit antiserum was diluted to make a dilution degree of 16000 times or more.

EXAMPLE 6

A. Production of Agglutination Test Plate

Two polyvinyl chloride plates with 96 U-shaped wells, each well having a capacity of 0.2 ml, were provided. To each well of each of the plates, 0.05 ml of a PBS solution containing protein A in a concentration of $1.0 \times 10^{-3}$ mg/ml was added. After 10 minutes, the PBS solution was poured out from the wells of the plate. Then, 0.05 ml of a fresh PBS solution was added to each well and again poured out from the wells to remove the remaining loose protein A from the wall surface of the wells. The plate was dried to produce a protein A-adhered test plate.

One test plate was stored at 4° C. for 7 days, and another test plate was stored at 25° C. for 7 days.

B. Agglutination Test

Using the protein A-adhered test plates produced in the above step, the agglutination test was made in a manner similar to that described in step B of Example 5. Satisfactory results, which were substantially the same as those of Example 5, could be obtained for each of the test plates stored at 4° C. and 25° C. for 7 days.

EXAMPLE 7

A. Production of Agglutination Test Plate

A polystyrene plate with 96 V-shaped wells, each well having a capacity of 0.3 ml, was provided. To each well of the polystyrene plate, 0.05 ml of a PBS solution containing protein G in a concentration of $1.0 \times 10^{-6}$ mg/ml was added. After 9 hours, the PBS solution was poured out from the wells of the plate. Then, 0.05 ml of a fresh PBS solution was added to each well and again poured out from the wells to remove the remaining loose protein G from the wall surface of the wells. The plate was dried to produce a protein G-adhered test plate.

B. Agglutination Test

On the protein G-adhered test plate produced in the above step, a rabbit antiserum for the Japanese Bemcephalitis virus used in step B of Example 2, rabbit antiserums for other viruses and a rabbit serum not-infected with a virus, were each added to the wells of the plate to make 0.05 ml of the antiserum or serum solution per well, after it was diluted with PBS. The dilution with PBS was repeatedly made so that twice the volume of the antiserum or serum solution was produced after each dilution. After 30 minutes, 0.05 ml of the PBS solution of the Japanese Bemcephalitis virus antigen-immobilized agglutinative composite particles produced in step B of Example 2 was added to each well. No agglutinated image was observed in any of the protein G-adhered test plates containing the rabbit antiserums for other viruses, or rabbit serum not-infected with a virus in the wells thereof. Contrary to this, in the protein G-adhered test plate containing the rabbit antiserum for the Japanese Bemcephalitis virus in the wells thereof, a clear agglutinated image was observed in the wells, until the rabbit antiserum was further diluted with the PBS to make a dilution degree of 8000 times; however, no agglutinated image was observed when the rabbit antiserum was diluted to make a dilution degree of 16000 times.

EXAMPLE 8

A. Production of Agglutination Test Plate

Two polyvinyl chloride plates with 96 U-shaped wells, each well having a capacity of 0.2 ml, were provided. To each well of each of the plates, 0.05 ml of a PBS solution containing both protein A in a concentration of $1.0 \times 10^{-5}$ mg/ml and protein G in a concentration of $1.0 \times 10^{-5}$ mg/ml was added. After 10 minutes, the PBS solution was poured out from the wells of the plate. Then, 0.05 ml of a fresh PBS solution was added to each well and again poured out from the wells to remove the remaining loose protein A and protein G from the wall surface of the wells. The plate was dried to produce a protein A/protein G-adhered test plate.

One test plate was stored at 4° C. for 7 days, and another test plate was stored at 25° C. for 7 days.

B. Agglutination Test

Using the protein A/protein G-adhered test plates produced in the above step, the agglutination test was made in a manner similar to that described in step B of Example 5. Satisfactory results, which were substantially the same as those of Example 5, could be obtained for each of the test plates stored at 4° C. and 25° C. for 7 days.

COMPARATIVE EXAMPLE 1

On a polystyrene plate with 96 V-shaped wells, each well having a capacity of 0.3 ml, a rabbit antiserum for the influenza virus used in step B of Example 1, rabbit antiserums for other viruses and a rabbit serum not-infected with a virus, were each added to the wells of the plate to make 0.05 ml of the antiserum or serum solution per well, after it was diluted with PBS. The dilution with PBS was repeatedly made so that twice the volume of the antiserum or serum solution was produced after each dilution. After 30 minutes, 0.05 ml of the PBS solution of the influenza virus antigen-immobilized agglutinative composite particles produced in step B of Example 1 was added to each well. No agglutinated image was observed in any of the test plates containing the rabbit antiserums for other viruses, or rabbit serum not-infected with a virus in the wells thereof. However, in the test plate containing the rabbit antiserum for the influenza virus in the wells thereof, a clear agglutinated image was observed in the wells, until the rabbit antiserum was further diluted with the PBS to make a dilution degree of 4000 times. However, an intermediate image which was indistinct and, accordingly, could not be judged to be an agglutinated image or not, was observed when the rabbit antiserum was diluted at a dilution degree of 8000 to 32000 times. No agglutinated image was observed when the rabbit antiserum was diluted at a dilution degree of 64000 times or more.

COMPARATIVE EXAMPLE 2

A. Production of Agglutination Test Plate

A polystyrene plate with 96 V-shaped wells, each well having a capacity of 0.3 ml, was provided. To each well of the polystyrene plate, 0.05 ml of a PBS solution containing protein A in a concentration of $1.0 \times 10^{-7}$ mg/ml was added. After 20 hours, the PBS solution was poured out from the wells of the plate. Then, 0.05 ml of a fresh PBS solution was added to each well and again poured out from the wells to remove the remaining loose protein A from the wall surface of the wells. The plate was dried to produce a protein A-adhered test plate.

B. Agglutination Test

On the protein A-adhered test plate produced in the above step, a rabbit antiserum for the Japanese Bemcephalitis virus used in step B of Example 2, rabbit antiserums for other viruses and a rabbit serum not-infected with a virus were each added to the wells of the plate to make 0.05 ml of the antiserum or serum solution per well, after it was diluted with PBS. The dilution with PBS was repeatedly made so that twice the volume of the antiserum or serum solution was produced after each dilution. After 30 minutes, 0.05 ml of the PBS solution of the Japanese Bemcephalitis virus antigen-immobilized agglutinative composite particles produced in step B of Example 2 was added to each well. No agglutinated image was observed in any of the protein A-adhered test plates containing the rabbit antiserums for other viruses or rabbit serum not-infected with a virus in the wells thereof. And, in the protein A-adhered test plate containing the rabbit antiserum for the Japanese Bemcephalitis virus in the wells thereof, a clear agglutinated image was observed in the wells, until the rabbit antiserum was further diluted with the PBS to make a dilution degree of 500 times. However, an intermediate image which was indistinct and, accordingly, could not be judged to be an agglutinated image or not, was observed when the rabbit antiserum was diluted at a dilution degree of 2000 to 4000 times. No agglutinated image was observed when the rabbit antiserum was diluted at a dilution degree of 8000 times or more.

We claim:

1. A test plate for an agglutination test, comprising:
   a plate with a plurality of wells formed thereon, each of said wells having directly adhered to a surface thereof at least one protein selected from the group consisting of a protein A and a protein G.

2. A process for the production of a test plate for an agglutination test, comprising:
   providing a test plate comprising a plate with a plurality of wells formed thereon;
   applying an amount of a protein solution containing at least one protein selected from the group consisting of a protein A and a protein G, directly to each of the wells of the plate;
   removing a portion of the applied protein solution from the wells; and
   drying the plate to obtain a test plate comprising the plate with wells having adhered directly to a surface of each well the at least one protein selected from the group consisting of protein A and protein G.

3. A process for the production of a test plate for an agglutination test according to claim 2, wherein a concentration of the sum of the at least one protein selected from the group consisting of protein A and protein G in said protein solution is at least $1.0 \times 10^{-6}$ mg/ml.

4. A process for the production of a test plate for an agglutination test according to claim 2, further comprising:
   leaving the plate at rest for a predetermined time, after applying the protein solution and before removal of the solution from the wells.

5. A process for the production of a test plate for an agglutination test according to claim 3, further comprising:
   leaving the plate at rest for a predetermined time, after applying the protein solution and before removal of the solution from the wells.

6. The test plate according to claim 1, wherein the plate is made of a plastic, and the at least one protein is adhered directly to the plastic.

7. The test plate according to claim 6, wherein the plastic is selected from the group consisting of polystyrene, polypropylene, and polyvinylchloride.

8. A process for the production of a test plate for an agglutination test according to claim 2, wherein the applied protein solution fills at least a bottom portion of each well.

9. A process for the production of a test plate for an agglutination test according to claim 2, wherein the wells have a capacity of 0.3 ml and wherein the amount of applied protein solution is about 0.05 ml.

10. A process for the production of a test plate for an agglutination test according to claim 2, wherein the plate is made of a plastic, and wherein the protein solution is directly applied to the plastic.

11. A process for the production of a test plate for an agglutination test according to claim 10, wherein the plastic is selected from the group consisting of polystyrene, polypropylene, and polyvinylchloride.

12. A test plate for an agglutination test produced by a process comprising:
    applying protein solution containing at least one protein selected from the group consisting of a protein A and a protein G, directly to each well of a test plate;
    removing a portion of the applied protein solution from the wells; and
    drying the plate to obtain a test plate comprising the plate with wells having adhered directly to a surface of each well the at least one protein selected from the group consisting of protein A and protein G.

13. A process for the production of a test plate for an agglutination test according to claim 12, wherein the applied protein solution fills at least a bottom portion of each well.

14. A process for the production of a test plate for an agglutination test according to claim 12, wherein the wells have a capacity of 0.3 ml and wherein the amount of applied protein solution is about 0.05 ml.

15. A test plate according to claim 12, wherein a concentration of a sum of the at least one protein selected from the group consisting of protein A and protein G in said protein solution is at least $1.0 \times 10^{-6}$ mg/ml.

16. A test plate according to claim 12, wherein the plate is made of a plastic, and wherein the protein solution is directly applied to the plastic.

17. A test plate according to claim 16, wherein the plastic is selected from the group consisting of polystyrene, polypropylene, and polyvinylchloride.

18. A test plate according to claim 12, wherein the process further comprises:
    leaving the plate at rest for a predetermined time, after applying the protein solution and before removal of the solution from the wells.

* * * * *